United States Patent [19]

Mony et al.

[11] 3,950,508
[45] Apr. 13, 1976

[54] PROCESS FOR OBTAINING PHARMACEUTICAL SUSTAINED RELEASES

[75] Inventors: Claude Mony; Geneviève Costes, both of Orleans, France

[73] Assignee: Laboratoires Servier, France

[22] Filed: May 7, 1973

[21] Appl. No.: 358,116

[30] Foreign Application Priority Data
May 10, 1972 France .............................. 72.16616

[52] U.S. Cl. ..................... 424/19; 424/22; 424/362
[51] Int. Cl.² ........................................... A61K 9/22
[58] Field of Search .............................. 424/19–22, 424/362

[56] References Cited
UNITED STATES PATENTS

| | | | |
|---|---|---|---|
| 2,980,589 | 4/1961 | de Grunigen | 424/362 |
| 2,993,836 | 7/1961 | Nash et al. | 424/19 |
| 3,079,303 | 2/1963 | Raff et al. | 424/35 X |
| 3,133,863 | 5/1964 | Tansey | 424/19 |
| 3,148,124 | 9/1964 | Gaunt | 424/22 |
| 3,453,360 | 7/1969 | Hill | 424/22 |
| 3,507,952 | 4/1970 | Rednick et al. | 424/22 |
| 3,728,445 | 4/1973 | Bardani | 424/22 |
| 3,773,920 | 11/1973 | Nakamoto et al. | 424/19 |
| 3,773,921 | 11/1973 | Sheth et al. | 424/19 |

*Primary Examiner*—Shep K. Rose
*Attorney, Agent, or Firm*—Gordon W. Hueschen

[57] ABSTRACT

Delayed action pharmaceutical tablets are prepared from admixtures of active ingredient with talc, ethyl cellulose and magnesium stearate tableting lubricant, with twice as much talc present as ethyl cellulose.

4 Claims, 7 Drawing Figures

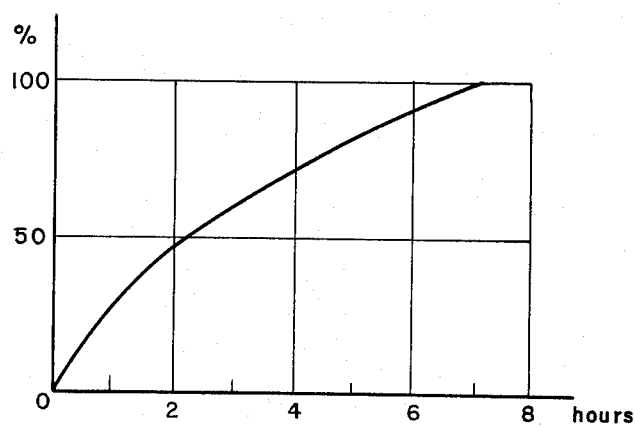
FIGURE 4
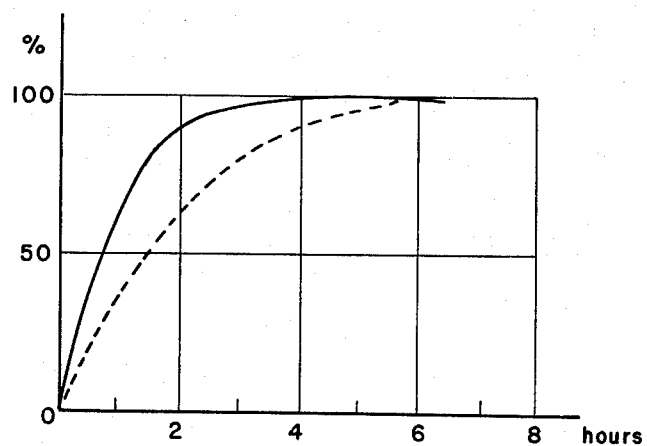
FIGURE 5
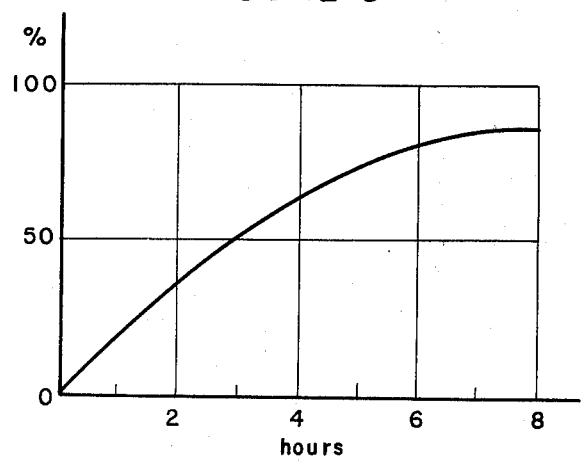
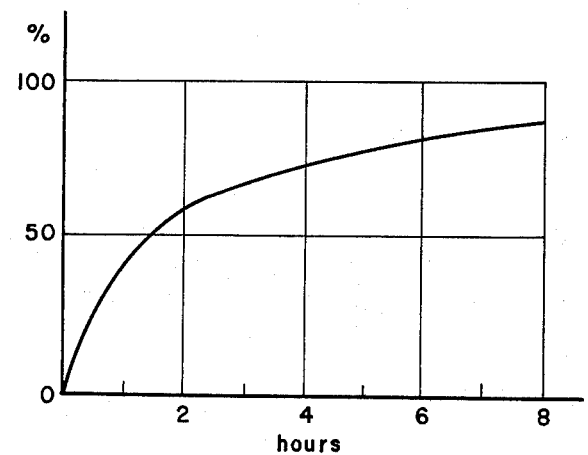

PROCESS FOR OBTAINING PHARMACEUTICAL SUSTAINED RELEASES

The object of the present invention is a process of obtaining delayed-action oral forms of medicines as well as the pharmaceutical forms thus obtained.

More particularly, the object of the present invention is a process of obtaining dry pharmaceutical forms for administration by mouth which have the characteristic of liberating the active principle or principles within a predetermined period of time.

This controlled release assures making available to the organism quantities of active principles, and therefore concentrations of drug such that the therapeutic action is optimalized.

By reducing intolerance and particularly gastric intolerance, the process of the invention can also improve the comfort of patients who are sensitive to certain drugs.

A very large number of processes which assure a prolonged action of release are already known. They are either chemical in nature, such as, for instance, the fixing of the active principle on ion-exchange resin, or pharmaceutical, such as coating with films of different thicknesses, dispersing in fatty or plastic matrices, or the producing of tablets with superimposed or concentric layers. All of these processes have in common the object of trying to obtain a release curve as a function of time which is sufficiently spread out that an effective concentration of the drug in the blood is maintained constant for a determinable period of time.

As a very general rule, the manufacture of the pharmaceutical forms in accordance with these processes is lengthy and difficult. It involves apparatus which is often complicated and frequently requires the employment of various artifices. The result of this is difficulty in obtaining good reproducibility from one manufacturing lot to the next. Furthermore, the processes cannot always be employed when the quantity of active principle per unit dose is relatively high since they involve a large number of factors (inert diluents, hydrophobic substances, swelling agent, adherence agent, etc.).

The process forming the object of the present invention has the considerable advantage that in order to obtain the pharmaceutical forms of delayed action it employs the conventional manufacturing and compressing equipment, and does so under favorable economic conditions.

Another advantage of the process in accordance with the invention resides in the possibility, based on an objective study of the formulation, of predicting the rate of release of the dose of active principle and determining it in advance with a high degree of precision.

The pharmaceutical forms obtained by the process of the invention therefore make it possible to assure the release of the active principle or principles with greater or lesser delay. These forms may furthermore comprise an additional layer which splits off more rapidly and releases the active principle more immediately. They may be in the form of aromatized or nonaromatized powders, granules contained in bags or in bottles, capsules, bare or coated tablets possibly made of concentric-layer or multi-layer tablets.

Another advantage of the process of the invention resides in the fact that said process can be used whatever the active dose of active principle necessary in order to obtain a physiological effect.

The liberation of this active dose has the very substantial advantage of being independent of the physical operating conditions, and particularly of the compression, and of the physiological condition of the patients; in particular, the pH of the gastric or intestinal juice affects it only slightly.

In accordance with the process of the invention, a dry pharmaceutical form is obtained by mixing one or more physiologically inert powders which are insoluble in water or almost insoluble in the fluids of the digestive tract with a binder which is also insoluble in water and soluble in organic solvents, said binder being intended to impart the necessary mechanical strength. The solid or liquid active principle or principles are incorporated in this mixture in the desired quantities and in suitable particle size.

The ratio of the insoluble powders to the active principle varies and may extend up to 10 to 1. Nevertheless, it preferably will not exceed 5 to 1. The amount of binder is preferably between 5 and 60 % of the active principle.

The mixture thus obtained is wetted with a solvent in which the binder is soluble, in order to make the mixture suitable for the granulating operations. After drying and crushing, tablets are produced by compression and can be coated or glazed as desired.

Other variants of the process of the invention — without these operations being limitative — may consist of a prior granulating of the active principle or a prior granulating of the physiologically inert insoluble powders, or the dissolving of the medicinal active principle in the wetting solvent, in the presence or absence of the binder. The mixture of powders can also be wetted by the solvent which already contains the binder in solution.

The formulation may also require the addition of diluents which are soluble or insoluble in water depending on the physical characteristics of the active principle, particularly when the latter is present in very small amount or in a liquid form.

When the active principle or principles are very soluble or insoluble in water or biological liquids or present very substantial differences in solubility between each other, particularly at different pH's, it may be necessary to add to them fillers which retard or favor the dissolving so as to regulate the joint liberation thereof.

The ratio of insoluble excipients to soluble active principles is a function of the physical characteristics of the active principles and the desired release times. Depending on these relative proportions, the tablet or dry form of the invention can liberate its medicinal dose without disaggregating and while retaining its geometrical shape, or with gradual disaggregation upon passage through the digestive tract.

The water-insoluble inert excipient is an inorganic or organic substance which is physiologically inert and therapeutically acceptable. It may consist, in particular, of complex natural silicates of aluminum or magnesium, mixed sodium silicates, calcium phosphates, kaolin, attapulgite, bentonite, montmorillonite, dimagnesium phosphate, trimagnesium phosphate, calcium sulfate, barium sulfate, aluminum oxide, aluminum hydroxide, magnesium oxide, magnesium hydroxide, silica, or kieselguhr.

Organic products such as natural polymers like cellulose, chitin, keratin and starches can also be employed.

The water-insoluble inert excipient must furthermore be of poor compressibility so that the speeds of release are independent of the force of compression and dependent only on the formula of the composition.

By way of example, there have been shown in the drawing release curves obtained with high doses of a water-soluble active principle (Compound A) as a function of time, the insoluble inert excipient being a mixed magnesium silicate. FIG. 1 shows that the percentage of release of the active principle as a function of time shows no significant variation whatever the compression.

Binders are selected from alkyl derivatives of cellulose which are insoluble in water and soluble in organic solvents. They are preferably cellulose ethers. They must satisfy the criteria of practical insolubility in water and solubility in non-polar solvents. Mention may be made, more particulary, of the ethyl celluloses sold by HERCULES POWDER under the names Ethyl Cellulose 10 to Ethyl Cellulose 400, depending upon the degree of substitution.

The fillers which favor the progressive release in the case of active principles which are of poor solubility in water or delay it otherwise may belong to any type of chemical class. They are selected as a function of their coefficient of solubility in water. One of the active principles may possibly play this role. As agent which favors the release of the active principles, mention may be made of soluble salts such as sodium chloride, sugars such as lactose, surface-active agents known as "wetting agents," such as "Tweens" or the "Spans" (registered trademarks for derivatives of partial esters of fatty acids and hexitol anhydrides).

The wetting solvent must be chemically inert with respect to the excipient. It must be capable of evaporating under conditions of temperature and pressure which are compatible with the industrial drying installations. It may also be a solvent for the active principle or principles. This solvent will preferably be an alkanol such has methanol, ethanol, isopropanol, a ketone, a linear or cyclic ether, an aromatic hydrocarbon, a chlorinated hydrocarbon, or a chlorofluorinated hydrocarbon, or else a mixture of these solvents.

The judicious use of the process in accordance with the invention makes it possible to obtain a pharmaceutical form of controlled action.

Due to the large number of possible embodiments, it is possible substantially to modulate the rate and time of the dissolving of the drug by varying the composition of the center, the coat, or the outer layer of the pharmaceutical form.

The active principles may belong to any class of therapeutic agents which can be administered by mouth. Mention may be made in particular of antibiotics such as tetracycline, penicillin V, or neomycin; hypnotics such as the barbiturates, methaqualone or mecloqualone; oral antidiabetics such as sulfamides or biguanides; antihistamines such as promethazine or phenyltoloxamine; bronchodilators such as theophylline or hydroxyethyl theophylline; vasoconstrictors such as ephedrine or isoprenaline or naphazoline; antitussants such as codeine or pholcodine, or else digestive enzymes such as pancreatin, enterokinase or a cellulase.

Another object of the invention is the dry drugs, administerable by mouth which are obtained by the process defined above.

Still another object of the invention is dry drugs, in particular in the form of bare or coated tablets, pills, granules, powders, tablets or capsules, whenever obtained by the process of the present invention.

The following examples serve to illustrate the invention. They in no way limit it.

BRIEF DESCRIPTION OF THE DRAWINGS

The invention will be more clearly understood and appreciated by reference to FIGS. 1 to 7 of the accompanying drawings, or graphical presentations. In FIGS. 1 to 7, the numbers along the horizontal represent time in hours, and the numbers along the vertical represent quantities dissolved.

EXAMPLE 1

Figure 1:
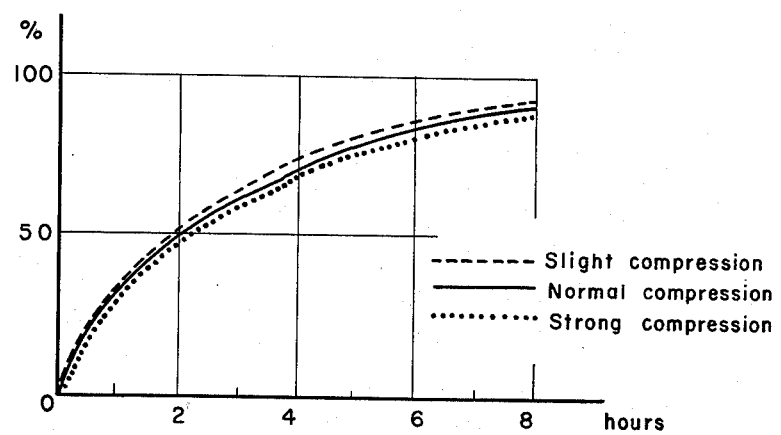

Study of the liberation of the active principle (Compound A) as a function of the force of compression. (See FIG. 1).

The excipient is a natural magnesium silicate; the binder is ethyl cellulose.

EXAMPLE 2

55 g Of sodium butobarbital are mixed with 15 g of ethyl cellulose and 176 g of talc. The mixture is then wetted with a sufficient amount of isopropyl alcohol, granulated, dried, crushed, and lubricated by addition of 4 g of magnesium stearate. Compression is then effected in such a manner as to obtain centers of a weight of 0.250 g, which are then coated to a final weight of 0.400 g.

Figure 2:
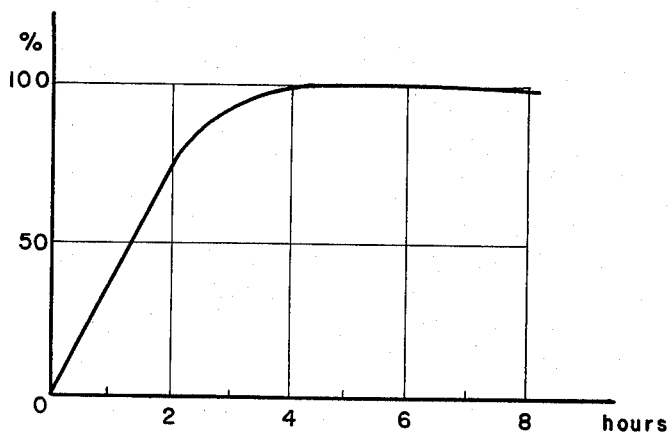

By effecting the dosaging of the quantities liberated as a function of time in accordance with the method of U.S.P. XVIII, it is possible to draw the curve of FIG. 2, the total release taking place in 5 hours. (See FIG. 2).

EXAMPLE 3

50 g Of ephedrine hydrochloride are mixed with 15 g of ethyl cellulose and 233 g of talc and then wetted with alcohol. After granulation, drying and crushing, the powder is lubricated by addition of 2 g of magnesium stearate and then compressed so as to obtain cores of a weight of 0.300 g which — if the operator desires — may then be coated in accordance with the conventional procedures.

Figure 3:
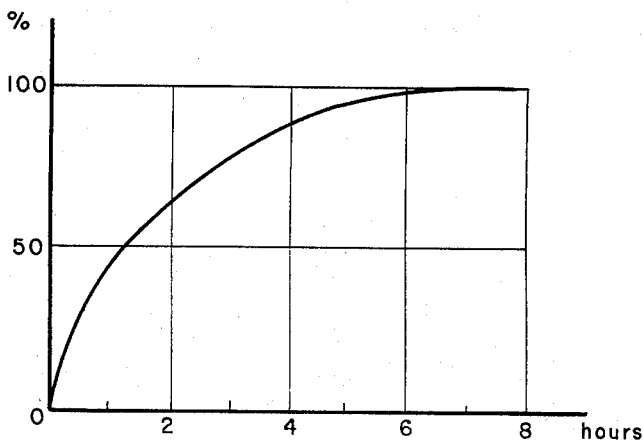

50 % Of the initial dose is liberated in 1 hour and 15 minutes, the entire active principle being released in 7 hours (See FIG. 3).

EXAMPLE 4

120 g Of fenfluramine are mixed with 446 g of talc and 30 g of ethyl cellulose (ethoxyl content 47.5 to 49 %). The mixture of powders is wetted with a sufficient amount of alcohol to obtain a plastic mass which is then dried at 50° C. After drying, the granulate is crushed and lubricated by the addition of 4 g of magnesiium stearate. The compressing is then effected on a suitable machine so as to obtain 2000 tablets of a weight of 0.300 g. The curve of FIG. 4 shows the release of the active principle. (See FIG. 4).

By way of example, by changing either the quality of the ethyl cellulose or the nature of the insoluble inert excipient, one can obtain the curves of FIG. 5 which have been drawn on basis of the analytical results obtained by the test set forth in U.S.P. XVIII. (See FIG. 5).

The administration of these tablets by mouth to dogs and the determination of the plasma level in blood samples show complete release of the medicinal principle and a prolonged action over 8 hours.

The lower curve corresponds to the use as a binder of an ethyl cellulose with an ethoxyl content of 49 %, while the upper curve corresponds to the use as binder of an ethyl cellulose having 44.5 to 45.5 % ethoxyl groups.

EXAMPLE 5

250 g Of 1-[methyl(benzo[d]1,3-dioxol-5-yl)]biguanidine hydrochloride are mixed with 10 g of ethyl cellulose, 5 g of polyvinylpyrrolidone (viscosity 45 centipoises for a 5 % aqueous solution at 25° C) and 323 g of talc. After this mixture has been wetted with the necessary amount of alcohol, the mass is granulated through a screen, and then dried and finally crushed. 12 g Of magnesium stearate are added to the granular powder thus obtained. Compressing is then effected in such a manner as to obtain about 1000 centers of a weight of 0.600 g, which are then coated to a final weight of 0.750 g. These tablets contain 0.25 g of active principle.

50 % Of the initial dose is thus liberated in 2 hours and 45 minutes, the release extending over more than 8 hours (See FIG. 6).

EXAMPLE 6

250 g Of tetracycline hydrochloride of given particle size are mixed with 40 g of ethyl cellulose and 25 g of polyvinylpyrrolidone (of a viscosity of 45 centipoises). After addition of 140 g of lactose and 203 g of talc, the mixture is wetted with a sufficient amount of alcohol and then granulated and dried. After crushing and the incorporating of 12 g of magnesium stearate, compressing is effected so as to obtain tablets of a weight of 0.670 g. The operator has the option of leaving them in this form or sugaring them so as to obtain tablets of 0.250 g of tetracycline hydrochloride.

50 % Of the tetracycline hydrochloride is released in 1 hour and 15 minutes, and 85 % in 7 hours (See FIG. 7).

We claim:

1. A process of preparing a dry, pharmaceutical delayed action composition suitable for oral administration in which at least one therapeutically active ingredient is dispersed in a vehicle or matrix of particulate talc, said talc being almost insoluble in the fluids of the digestive tract and the particles thereof being bound together by a binder consisting of a solid, water-insoluble, organosoluble, ethyl cellulose which comprises preparing a dry mixture by mixing in the dry powdered state the therapeutically active ingredient, the talc, and the binder, in the proportions of about 1 to 5 parts of talc for each part of active ingredient and about 16 and 59 parts of dry mixture for each part of binder, with the further proviso that there be present at least twice as much talc as ethyl cellulose, wetting the powder mixture with solvent in which the binder is soluble and in which the talc is insoluble in an amount just sufficient to insure granulation, and then granulating the resultant wetter powder mixture, drying the granules, incorporating therein as a tableting lubricant from about ⅔ to 2% of magnesium stearate, and tableting the resulting mixture.

2. A process according to claim 1, wherein at least one additional physiologically inert, water-soluble ingredient is added to the mixture of ingredients to regulate the diffusion of the active substances therein, selected from the group formed of polyvinylpyrrolidone and lactose.

3. A process according to claim 1, wherein the water-insoluble ethyl cellulose is an ethyl cellulose containing from 44.5 to 49 percent ethoxyl groups.

4. A pharmaceutical composition possessing delayed action properties when administered by the oral route, prepared by the process of claim 1.

* * * * *